(12) United States Patent
Brewer et al.

(10) Patent No.: US 6,870,234 B2
(45) Date of Patent: Mar. 22, 2005

(54) OPTICALLY- AND ELECTRICALLY-ADDRESSABLE CONCENTRATORS OF BIOLOGICAL AND CHEMICAL MATERIALS

(75) Inventors: Peter D. Brewer, Westlake Village, CA (US); David Chow, Newbury Park, CA (US)

(73) Assignee: HRL Laboratories, LLC, Malibu, CA (US)

( * ) Notice: Subject to any disclaimer, the term of this patent is extended or adjusted under 35 U.S.C. 154(b) by 138 days.

(21) Appl. No.: 10/230,968

(22) Filed: Aug. 29, 2002

(65) Prior Publication Data

US 2003/0066999 A1 Apr. 10, 2003

Related U.S. Application Data

(60) Provisional application No. 60/316,655, filed on Aug. 30, 2001.

(51) Int. Cl.⁷ .............................................. H01L 27/14
(52) U.S. Cl. ........................................ 257/414; 257/15
(58) Field of Search ........................... 257/414, 15, 431

(56) References Cited

U.S. PATENT DOCUMENTS

| | | | |
|---|---|---|---|
| 5,605,662 A | * | 2/1997 | Heller et al. ................ 422/68.1 |
| 5,674,698 A | | 10/1997 | Zarling et al. .............. 435/7.92 |
| 5,719,392 A | | 2/1998 | Franzen ...................... 250/282 |
| 6,277,651 B1 | * | 8/2001 | Groger et al. .............. 436/518 |

* cited by examiner

*Primary Examiner*—Douglas Wille
(74) *Attorney, Agent, or Firm*—Ladas & Parry LLP

(57) ABSTRACT

A concentrator for detecting biological and/or chemical materials in an environment. The concentrator comprises an engineered superlattice structure having alternating layers of elemental, binary or ternary group III-group V, or group IV-group IV semiconducting materials. A method for detecting biological and/or chemical materials in an environment using the concentrator. The method comprising exposing the concentrator to the biological and/or chemical materials in an environment and activating the superlattice structure optically or electrically followed by the detection of the biological and/or chemical materials.

13 Claims, 5 Drawing Sheets

OPTICALLY- AND ELECTRICALLY-ADDRESSABLE CONCENTRATORS OF BIOLOGICAL AND CHEMICAL MATERIALS

CROSS-REFERENCE TO RELATED APPLICATIONS

This application claims priority under 35 U.S.C. §119(e) to co-pending U.S. Patent Application No. 60/316,655 (filed on Aug. 30, 2001) entitled "OPTICALLY-ADDRESSABLE CONCENTRATORS OF BIOLOGICAL AND CHEMICAL MATERIALS," the contents of which are hereby expressly incorporated herein in their entirety by this reference.

I. BACKGROUND

1. Field

This invention relates to the field of compact devices for remotely detecting the presence of biological and/or chemical materials using the reversible binding of specific molecules onto a superlattice concentrator structure in order to quickly manipulate and identify these molecules.

More particularly, it pertains to the use of a new class of solid-state concentrators of biological and/or chemical agents made from engineered Group III–V semiconductor superlattice structures, surface binding properties of which can be controlled and manipulated by optical illumination or other means, such as electrical biasing.

2. Description of the Related Art

Early detection and identification of the presence of biological agents is important because it would allow initiation of rapid evacuation of an affected area, start of immediate decontamination procedures, and provide needed information for medical treatment of personnel.

There exist a large number of known detection methods used to identify chemical and biological materials. As discussed below, all currently used methods are limited in terms of sensitivity, response time, possibility of miniaturization, or a combination thereof. The most commonly used methods are as follows:

(a) Gas and Liquid Chromatography. According to these analytical techniques, an analyzed blend is separated based on the Nernstian distribution of the components of the blend between two phases.

In the case of gas chromatography, the blend is first evaporated and then directed to a solid adsorbent where the blend is separated. In the case of liquid chromatography, a liquid adsorbent is used for separation.

After the separation, the individual components, including biological agents, are detected, usually using the differences in the components' heat transfer properties. Although chromatographical methods are quite sensitive (from the low parts per million (ppm) range for gas chromatography to the moderate ppm range for liquid chromatography), they have serious disadvantages. The response times for these methods are long and portability is very limited because it is difficult to miniaturize the equipment.

(b) Gel Electrophoresis. According to this method, particles of a gel (disperse phase) move in the dispersion medium under the influence of an electric field. The detection of an agent, including a biological and/or chemical agent, is based on the principle that the speed of the particles is proportional to the intensity of the electric field. The electric field causes the change of the electric potential on the border between the gel phase and the dispersion medium and this change is related to the nature of the gel particles.

Although the gel electrophoresis-based concentrator can be made portable, the method has a low sensitivity and very long response times leading to only limited use of the method for detection of biological and/or chemical agents.

(c) Optical Absorption and Raman Spectroscopy. The method of optical absorption is based on the transition of electrons in an excited state as a result of absorption of energy by the analyzed molecules in ultraviolet, visible and near infrared areas of the spectrum (between about 120 and 1,000 nanometers).

After such energy has been absorbed, wide-band spectra are obtained and the analyzed molecule is identified.

In Raman spectroscopy, the analyzed substance is irradiated with monochromatic radiation. When a beam of photons strikes the molecule, some photons undergo inelastic or Raman scattering and such Raman scattered photons have different frequencies and produce a spectrum of frequencies in the scattered beam that constitute the Raman spectrum of the analyzed molecule. This spectrum is used for the identification of the sample.

Even though both the optical absorption method and the Raman spectroscopy method provide a fast response time, sensitivity of both is low, and portability is limited. In addition, in the optical absorption method, multiple compounds absorb the energy, thus producing a multiplicity of the resulting spectra and obfuscation of the molecule being sought.

(d) Fluorescence Spectroscopy (Tags). According to this method, visible or ultraviolet radiation (at wavelengths between about 200 and 700 nanometers) is first absorbed by the analyzed specimen. Thereafter, the excited molecules return to the normal condition. This process is accompanied by the emission of radiation. The emission spectrum of the radiation is thus obtained and used to identify the molecule.

The fluorescence spectroscopy method has fast response time and is amenable to designing a portable instrument. However, the method has only moderate sensitivity due to background noise contamination.

(e) Upconverting Phosphor. This method provides good background rejection and has fast response times. Making a portable instrument for this method is also possible. According to this method, uniform submicron microspheres of upconverting phosphors (UCPs) are synthesized and coated with biologically active probes, such as antibodies. UCPs are materials that emit visible light upon excitation with near-infrared light. Functionalized UCP particles are used to selectively bind to captured target antigens. Visible emission following exposure to IR radiation indicates a target.

However, this method must be interfaced with pre-processing techniques, which limits the applicability and usefulness of UCPs.

(f) Mass Spectroscopy. The method of mass spectroscopy is based on the ionization of a molecule, typically by bombarding the molecule with electrons having energy between about 50 and 70 electron-volts. The process takes place in a high vacuum environment (at least $10^{-6}$ torr vacuum is required). The ions created as a result are accelerated in an electric field and separated in a magnetic field according to their mass. A mass spectrum is then created showing the mass-to-charge ratios for various ions created as a result of the fragmentation of the molecule due to the bombardment and the relative amounts of such ions. This spectrum is used to identify the original molecule.

The sensitivity of this method is high, the response time is fast and miniaturization of the instrument and portability is possible. However, the method requires expensive and fragile equipment necessary to create and maintain a very high vacuum. The method requires high power consumption and the equipment is susceptible to clutter problems.

(g) Ion Mobility Spectrometry. This method is highly sensitive, has fast response time and the instrument can be portable. Ion Mobility Spectrometry (IMS) involves the ionization of molecules and their subsequent temporal drift through an electric field. Analysis and characterization are based on separations resulting from ionic mobilities rather than ionic masses; this difference distinguishes IMS from mass spectroscopy. However, serious problems of cross-coupling of the signal with temperature and pressure limit its applicability for detection of biological and/or chemical agents.

As far as the instruments are concerned, there exist a number of current generation sensors used in detection of biological and/or chemical agents. Many of these sensors are constructed with a sensor transducer in combination with a biologically active surface.

A key element of these point detection systems involves the immobilization of the biological and/or chemical agent. This issue is very important for binding, isolating and concentrating the biological and/or chemical agent on the transducer as well as for maintaining the agent's structure, activity, and stability. Biological species of interest include various toxins, viruses, rickettsia, fungi, parasites, bacteria, or uniquely identifiable components or byproducts (DNA, RNA, proteins, sugars, etc.).

Typically, the surfaces on which biological agents are immobilized, comprise antibodies of a particular species of interest for trapping the particular biological agent (antigen). These surfaces are integrated into a transducer for sensing. Examples of such devices comprise surface acoustic wave (SAW) resonators, cantilever resonators, surface plasmon resonance reflectors, and fiber-optic based sensors that are coated with immobilizing surfaces.

The antibody-antigen (biological molecule) binding is irreversible, which both benefits these detection methods and causes complications. The limitations of irreversible binding comprise baseline drift, saturation, and contamination of the sensor surfaces. Current generation point detection systems are often dependent on time-consuming molecular amplification processes that are needed to increase the signature of the pathogen or agent.

There is a need to have compact, low cost remote concentrators of biological and/or chemical species which:
(a) are very sensitive, compact in size, and able to detect very small quantities of the compound in question;
(b) have fast response times;
(c) are portable and compact; and
(d) are more reliable and have lower false alarm rates than currently available sensors.

There exists no known prior art for compact concentrators satisfying all these enhanced requirements. Yet the need for such is acute. For the foregoing reasons, there is a necessity for a compact low-cost sensor for detection of very low amounts of biological and/or chemical substances. The present invention discloses such concentrators which can serve to bolster the performance of any existing detection method by concentrating the bio- or chemical-agent before analysis.

II. SUMMARY

This invention discloses a new class of solid-state concentrators of biological and/or chemical agents made from engineered, superlattice structures, preferably based on group III-group V or group IV-group IV semiconducting materials. The surface binding properties of such superlattice structures can be controlled and manipulated, preferably, by optical illumination, or by other means, such as, for instance, electrical biasing.

The surfaces of the superlattice devices (edges of the structures) are designed to selectively complement the charge distributions (structural-chemical features) of a specific biological and/or chemical molecule.

The present invention takes advantage of the lengthwise similarity between the thickness of a superlattice layer and the typical distance between bonding sites of many biological and/or chemical molecules, as well as between the overall thickness of the superlattice structure and typical overall lengths of such biological and/or chemical molecules. The lengths of the biological molecules are typically within a range between about 1 and 5 micrometers.

Indeed, the selective binding of the biological and/or chemical agents by the method disclosed in this invention relies significantly on the similarity in length scale between biological and/or chemical agents or biological molecule's (DNA, RNA, proteins, and the like) and engineered superlattice structures. In both cases, the fine resolution charge distributions lie in the 3–10 Angstroms scale and the coarse lengths are in the 2–10 micrometers range. For example, the dimensions between base pairs that serve to bind the individual strands of DNA are on the order of 5 Angstroms.

Similarly, engineered superlattice structures can be fabricated with isolated layers on this length scale.

Illumination of the devices is preferably used to control and activate carriers (electrons and holes) in specific layers in the superlattice stack. The illumination results in a unique charge distribution on the edge of the stack.

Superlattice structures are designed in such a way that the above-mentioned illumination-induced surface charge distribution controls the binding properties for a particular biological and/or chemical molecule.

The optical control of the surface binding-properties allows the devices to quickly, selectively, and reversibly trap and release biological and/or chemical agents. The selective binding and detachment forms the basis of the enhanced detection scheme which is a subject matter of the present invention.

According to a first aspect of the invention, a concentrator of biological or/and chemical materials is provided, the concentrator comprising an engineered superlattice structure, the structure fabricated out of semiconducting materials, preferably group III-group V semiconducting materials, or group IV-group IV semiconducting materials. Preferably, the superlattice structure comprises alternating layers of elemental group and binary group or ternary group semiconducting materials; or alternating layers of binary group and binary group or ternary group materials. For example, in a superlattice structure comprising alternating layers of elemental group and binary group or ternary materials, the elemental group materials comprise group IV semiconducting materials. If, for example, the superlattice structure comprises alternating layers of binary and ternary group materials, the binary semiconducting materials may comprise gallium-arsenide, gallium-phosphide, silicon-germanium, silicon-carbon, gallium-antimonide, indium-arsenide, indium phosphide, indium-antimonide, aluminum-arsenide, or aluminum-antimonide, and the ternary semiconducting materials may comprise aluminum-gallium-arsenide, silicon-germanium-carbon, indium-gallium-phosphide, indium-gallium-arsenide, indium-aluminum-arsenide, aluminum-gallium-arsenide, or aluminumgallium-antimonide. Those skilled in the art will understand that the materials other than those listed above may comprise the binary group or ternary group materials that may be used. In an alternative embodiment, the superlattice structure may comprise alternating layers of silicon and silicon-germanium, silicon and silicon-carbon, silicon and silicon-germanium-carbon, or silicon-germanium and silicon-carbon semiconducting materials.

According to a second aspect of the invention, a method for detecting biological and/or chemical materials comprises steps of providing a concentrator of biological and/or chemical materials comprising an engineered superlattice structure fabricated out of semiconducting materials, exposing the concentrator to the biological and/or chemical materials, trapping and concentrating the biological and/or chemical materials on a surface of the superlattice structure by activating the superlattice structure, detecting the biological and/or chemical materials, and releasing the biological and/or chemical materials from the superlattice structure.

III. BRIEF DESCRIPTION OF THE DRAWINGS

The features and advantages of the present invention will become better understood with regard to the following description, appended claims, and accompanying drawings.

IV. DETAILED DESCRIPTION

1. The Invention in General.

Figure 1:
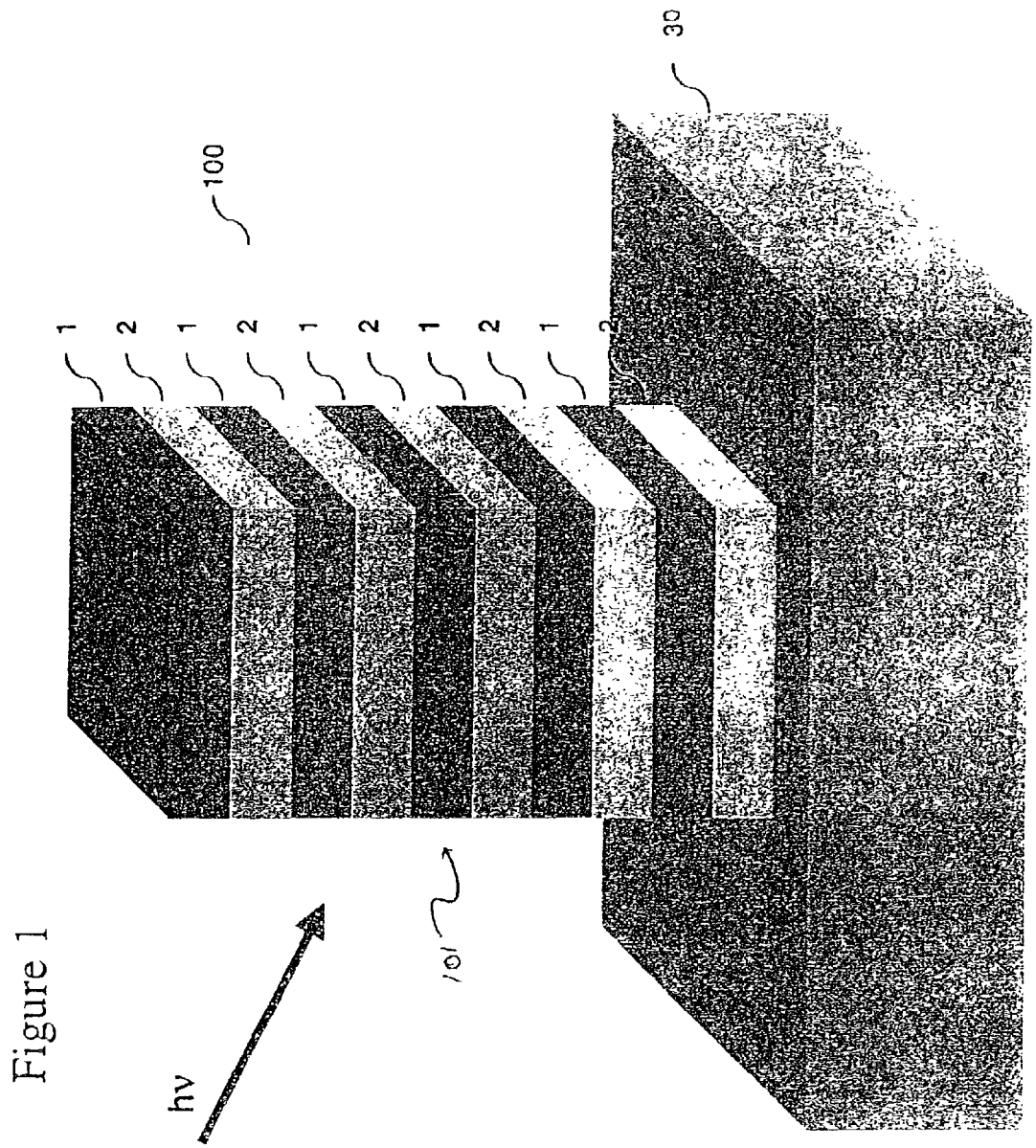
FIG. 1 is a schematic diagram showing a cross-sectional view of a preferred multi-layer structure designed to capture specific biological and/or chemical molecules.

The concentrator of this invention preferably comprises a multi-layer engineered superlattice having alternating layers made of preferably binary group III-group V semiconducting materials and of preferably ternary group III-group V semiconducting materials. FIG. 1 shows a cross-section of a gallium-arsenide (GaAs)/aluminum-gallium-arsenide ($Al_xGa_{1-x}As$) multi-layer structure which is a preferred superlattice, concentrator structure designed to capture a specific biological and/or chemical molecule. In $Al_xGa_{1-x}As$, x is a mole fraction of Al in aluminum-gallium-arsenide, x preferably being within a range of between about 0.16 and about 0.8. (For AlGaAs x is about 0.16).

As shown on FIG. 1, the superlattice structure 100 comprises alternating layers 1 of GaAs and 2 of $Al_xGa_{1-x}As$. The structure 100 is preferably grown by molecular beam epitaxy (MBE). The layers 1, 2 may be fabricated on a substrate 30. MBE methods are known to those reasonably skilled in the art of making semiconductor devices.

The superlattice structure usually comprises between about 50 and about 1,000 alternating layers 1 and 2, each layer typically having a thickness of between about 3 and about 10 Angstroms. The total thickness of the entire superlattice 100 is typically between about 1 and about 5 micrometers.

The preferred geometry of the superlattice structure 100 is such that the edges 101 of the superlattice are exposed to the contaminated environment. In order to achieve this goal, standard etching methods known to those skilled in the art are employed, including wet-chemical etching and reactive ion etching techniques. Arrays of mesa or grading type structures are preferred structures allowing significant surface areas of the edges 101 to be accessed by the contaminated environment.

As will be discussed below, the superlattice structure is used for selective binding and detecting of phosphoglyderides, DNA and RNA strands. For simple organisms, such as bacteria or bacteriophages, the number of nucleotides in their DNA strands is typically within a range between tens and hundreds of thousands, and certainly less than two million.

The superlattice required for detection of such simple organisms is capable of being manufactured by the MBE method. The MBE is a preferred method of manufacturing of the superlattice. In addition, a Metal Organic Chemical Vapor Deposition (MOCVD) method, known to those skilled in the art, can be also used as another preferred method of manufacture.

In addition to the preferred $GaAs/Al_xGa_{1-x}As$ structure, other group III-group V-based superlattice systems can be used, as long as the materials of such alterative systems can sustain a surface charge; that is, these materials should not exhibit surface depletion effects.

The way the superlattice is used to reversibly bind and detect particular biological and/or chemical agents will be discussed in detail, infra, by way of the following Examples. Examples 1 and 2 follow directly. It should be mentioned that Examples 1 and 2 are given only for illustrative purposes and should not be construed in any limiting way. In fact, those reasonably skilled in the art will understand that the method can be used for detecting other biological and/or chemical agents as necessary.

2. Preferred Biological Molecules Detectable by the Method of the Invention.

The method and the superlattice of this invention are suitable for detection of various biological materials, preferably, strands of DNA and RNA and phosphoglycerides, as described below in Examples 1 and 2.

EXAMPLE 1

Selective Binding of Strands of Deoxyribonucleic and Ribonucleic Acids (DNA and RNA).

Figure 3:
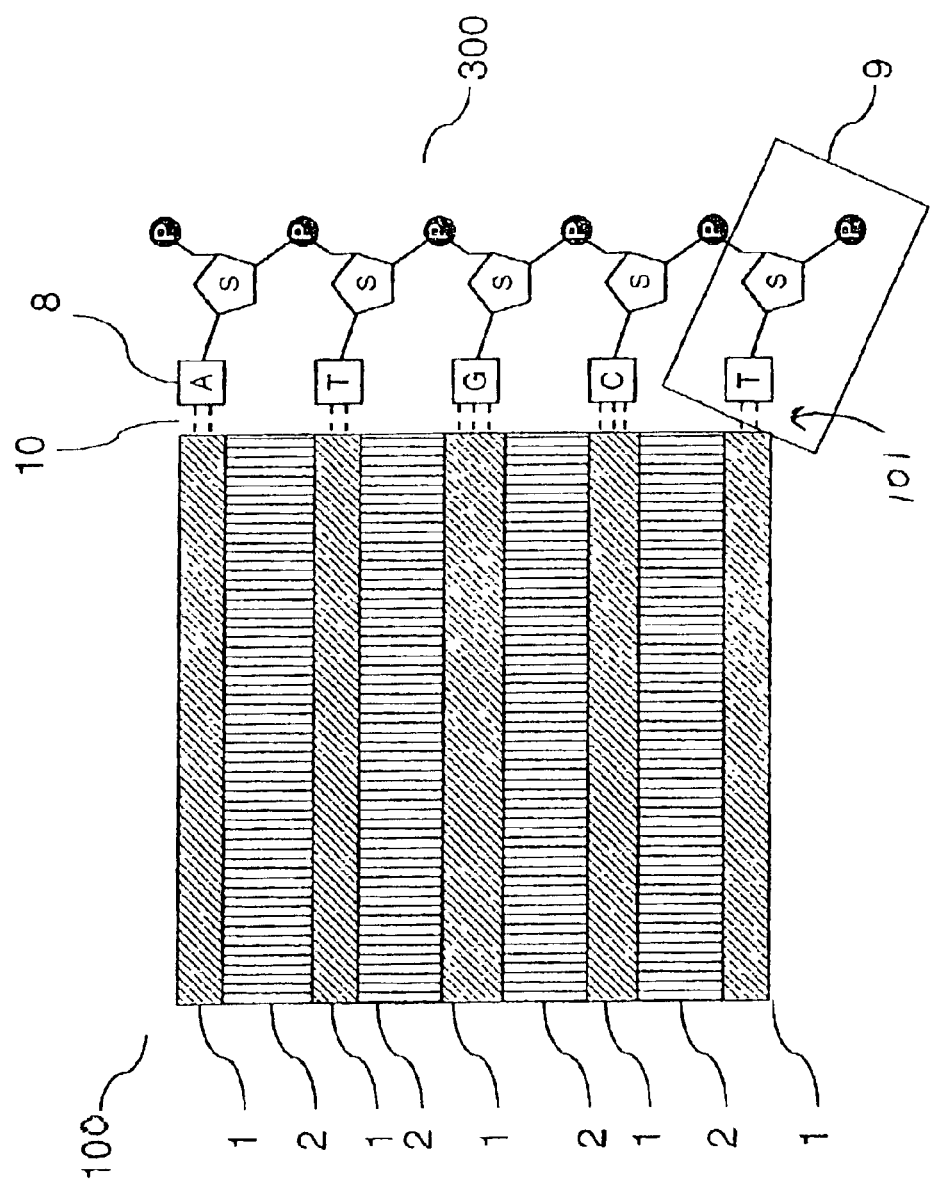
FIG. 3 is a schematic diagram illustrating the similarity of the length scale and selective binding between an individual strand of DNA and an engineered superlattice structure.

FIG. 3 illustrates the similarity of the length scale and selective binding between an individual DNA strand and an engineered superlattice structure 100. The DNA strand 300 comprises a sugar-phosphate backbone 7 and a base 8. As seen from FIG. 3, nucleotide 9 of the DNA strand attaches itself to the superlattice layers 1 and 2 at the edge 101 of engineered superlattice structure 100. Hydrogen bonds 10 are utilized in order to achieve such attachment.

Optical addressing, e.g., illuminating of the superlattice stack 100, to be discussed below, is used to activate specific layers that result in a unique surface charge distribution that complements the binding sites of a particular biomolecule. Binding of the biomolecule to the surface, as mentioned above, utilizes low energy hydrogen bonds 10.

The fine resolution charge distributions lie in the 3–10 Angstroms scale and the coarse lengths are in the 2–10 micrometers range. For example, the dimensions between base pairs that serve to bind the individual strands of the DNA are on the order of 5 Angstroms.

In implementing the superlattice structure for detection of nucleotide sequences, complementary charge sequences are generated in the superlattice structure by one of a number of the methods, such as electrical biasing or, preferably, by illuminating the surface of the superlattice, as described below. Such charge sequences match the overall DNA or RNA molecule.

The fine features of the charge distributions are generated to bind each of the bases found in DNA, such as, e.g., adenine (A), thymine (T), guanine (G), and cytosine (C). Each of these bases possesses a unique bonding or charge arrangement. The complementary charge sequences on the superlattice are generated to mimic the charge distributions as found in nature. These naturally occurring distributions are such that the charge distribution of adenine complements that of thymine, and that of cytosine-guanine.

EXAMPLE 2

Phosphoglycerides as Keys to Detection of Cell Membranes

Cell membranes contain distinguishing features enabling selective binding and general organism identification. They make up as much as 80% of the mass of their respective cells and serve as aqueous separation barriers as well as structural bases to which certain kinds of enzymes and transport systems are bound. Most cell membranes are known to contain 40% lipids and 60% proteins. A basic structure of a cell membrane is schematically depicted on FIG. 2.

Figure 2:
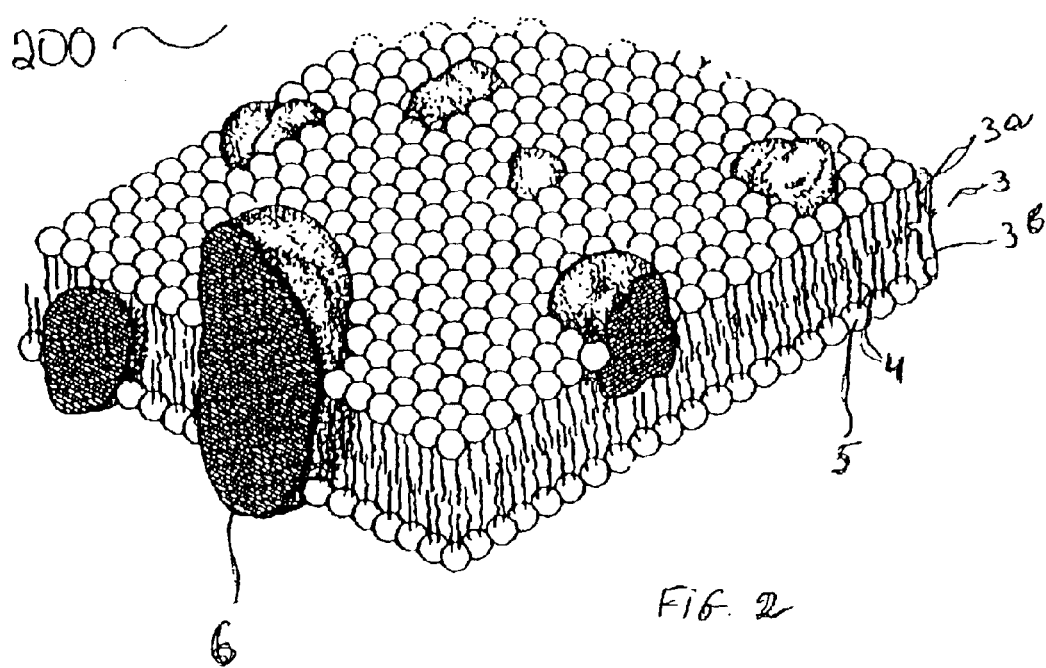
FIG. 2 is a schematic diagram showing a structure of a cell membrane with a lipid bi-layer.

The membrane 200 shown on FIG. 2 comprises a fluid phospholipid bilayer 3 (comprising phospholipid monolayers 3a and 3b) of mixed polar lipids, with their hydrocarbon-chain tails 4 oriented inwardly to form a continuous hydrocarbon phase and their hydrophilic, polar heads 5 oriented outwardly. In this bilayer 3 individual lipid molecules can move laterally, giving the bilayer 3 fluidity, flexibility and a characteristically high electrical resistance. Cell membrane 200 binds proteins 6.

As is clear from the above discussion, phosphoglycerides, as a large class of complex lipids, form a major component of cell membranes. Therefore, the detection of phosphoglycerides is a key to detecting the presence of cell membranes, leading in turn to the identification of a biological and/or chemical molecule. As will be subsequently discussed, it is the selective binding of the polar head groups 5 to the concentrator surface of this invention, that forms the basis of this embodiment of the present invention.

As mentioned above, phosphoglycerides possess a polar head group 5 and a hydrophobic, non-polar tail 4. Various kinds of phosphoglycerides differ in their respective sizes, shapes and electric charges of the polar head groups 5, due to their differences in functional groups. As a result, charge distributions, both spatially-wise and intensity-wise, are different for polar head groups 5 of each phosphoglyceride, enabling selective binding of particular phosphoglycerides to specially engineered surfaces 101 with particularly tailored charge distributions. The most abundant phosphoglycerides found in higher plants and animals are phosphatidylethanolamine (PEA, a polar head of which is shown in formula I below), and phosphatidylcholine (PC, a polar head of which is shown formula II below). PEA and PC are the major components of most animal cell membranes.

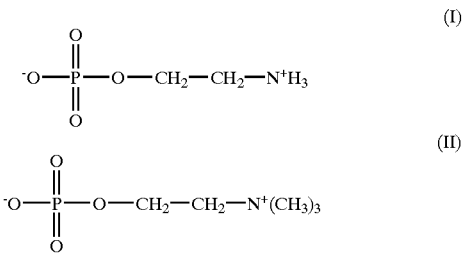

For bacteria, the most important phosphoglycerides are cardiolipin, also known as diphosphatidylglycerol (CL, a polar head of which is shown in formula III below), phosphatidylglycerol (PDG, not shown), and 0-aminoacylphosphatidylglycerol (APDG, not shown)

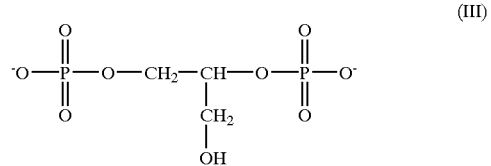

For all the phosphoglycerides discussed above, the open bonds on hydroxyls of the phosphoric residues lead to the hydrophobic tail portions of the particular phosphoglyceride and are connected to the position "3" of 1,2-diacylglycerol.

The charge characteristics of the heads of the phosphoglycerides are known. Typically, there are two to three fully charged sites, either possessing an extra electron (negatively charged nucleophilic sites) or one-electron deficient (positively charged electrophilic sites), or dipole sites having both. The nucleophilic sites are located on oxygen atoms as shown in formulae (I), (II), and (III). The electrophilic sites, in cases of PEA and PC, are located on the quasi-quaternary ammonium-type atom of nitrogen.

The method of this invention utilizes the fact of the length-scale similarity between the thicknesses of the superlattice layers and the typical distance between bonding sites on the polar heads of individual phosphoglyceride molecules (Angstrom scale) as well as distances between neighboring lipid molecules (nanometer scale).

For instance, the charged sites mentioned above are uniquely spatially separated and the distance between the charged sites in CL, PEA, and PC was previously measured by prior researchers to be about 7.6 Angstroms for CL (formula III), about 6.0 Angstroms for PEA (formula I), and about 4.9 Angstroms for PC (formula II). In addition to the charged sites discussed above, many phosphoglycerides heads also possess polarized sites due to the presence of chemical groups with a permanent dipole moment, for instance, hydroxyl groups —OH or carbonyl groups C=O.

It should be borne in mind that, as is clear from the preceding discussion, all of the above-mentioned charged sites and polarized dipole structures are parts of the lipid molecules forming cell membranes. Hence, these charged fragments and dipole fragments attract and orient the lipid molecules towards the engineered surface 101 of the superlattice structure of this invention and bind the lipid molecules to this superlattice's surface.

Of those charged and dipole fragments mentioned above, positively charged sites are attracted to the electron-rich areas of the activated surface of the superlattice structure of this invention, and negatively charged sites—to the electron-deprived areas. Thus, the phosphoglycerides are bound to the surface and retained there, followed by the detection to be discussed subsequently.

The binding of the phosphoglyceride molecules to the surface can be illustrated as shown on FIG. 3 for the DNA strand, except that the bonding in case of phosphoglycerides occurs due to the attraction of the charged sites to the electron-rich areas of the activated surface of the superlattice structure of this invention, as mentioned above, rather than due to the formation of hydrogen bonds, as occurs in case of the DNA strands. The phosphoglyceride molecules are attracted to, and bond to the GaAs portion of the superlattice.

3. Detection.

Using the above-described superlattice structure 100 for determination of the presence and the amount of biological and/or chemical molecules of a particular kind includes the steps of attracting the molecules by the superlattice structure, concentrating of the molecules on the surface of the superlattice, the detection of the molecules, and their release. It should be understood, that the sensitivity of the method depends solely on the sensitivity of detection method chosen. Even if a very minimal amount (as low as a few parts per trillion) of the biological and/or chemical materials is trapped by the superlattice, it still can be detected, using suitably sensitive detection techniques.

In general, the concentrator is first exposed to the environment containing the biological and/or chemical material being detected. Usually, such environment is a liquid, for instance, a solution containing the biological and/or chemical material; however, detection in a gas phase, for example, in the air, is also possible.

Next, the individual layers in the superlattice structure are preferably activated by shining particular wavelengths of light (shown as "hv" on FIG. 1) onto the superlattice structure 100, to produce a complex charge distribution on its surface. Besides the activation of the individual layers by optical means, any other alternative method of activation can be used. Such methods of activation are known to those skilled in the art. An example of such an alternative method is the activation of the individual layers by electrical biasing, as subsequently discussed.

The charge distribution in case of optical activation of the individual layers will depend on the optical absorption properties of the individual layers of the superlattice 100 and can be modified by varying the thicknesses and compositions of those layers, according to a chosen design.

It should be understood that in order to trap a particular kind of a biological and/or chemical molecule, a surface charge distribution that is specifically suited for this particular kind of the biological and/or chemical molecule is required. In other words, the surface charge distribution produced by activating the individual layers in the superlattice must be specifically tailored to a particular biological and/or chemical molecule that is to be detected.

Stacking the layers with pre-selected absorption characteristics combined with the specific doping of the layers, is used to produce such specific complex charge distributions. As a result of producing such charge distributions, particular biological and/or chemical molecules are attracted to the surface of the superlattice and are trapped thereupon as described in detail hereinabove.

The period of the exposure of the superlattice structure to light is between a few seconds to a few minutes, depending, inter alia, on the kind of the biological and/or chemical molecule being detected, and on its concentration.

Generally, the time of the exposure should be such as to permit the amount of the biological and/or chemical substance sufficient for the detection to be accumulated on the surface of the superlattice structure 100.

In the case of the phosphoglycerides and the DNA/RNA strands, the time of exposure will be between about 1 second and a few minutes, depending on the concentration of the phosphoglycerides or the DNA/RNA strands in the environment.

Describing particular details of the optical activation of the surface of the superlattice structure 100, it should be borne in mind that in order to achieve such activation, the energy gap (the difference between the valence band potential and the conductance band potential) must be overcome. From this basic requirement it follows, that the optically generated free carriers in the superlattice structure are captured by the GaAs layers and not by the $Al_xGa_{1-x}As$ layers due to the smaller energy gap of GaAs relative to $Al_xGa_{1-x}As$. Therefore, it is the GaAs layer that must be excited, and not the $Al_xGa_{1-x}As$ layer, because the latter layer just serves as an insulator of the GaAs layer and does not itself trap any molecules.

Figure 4:
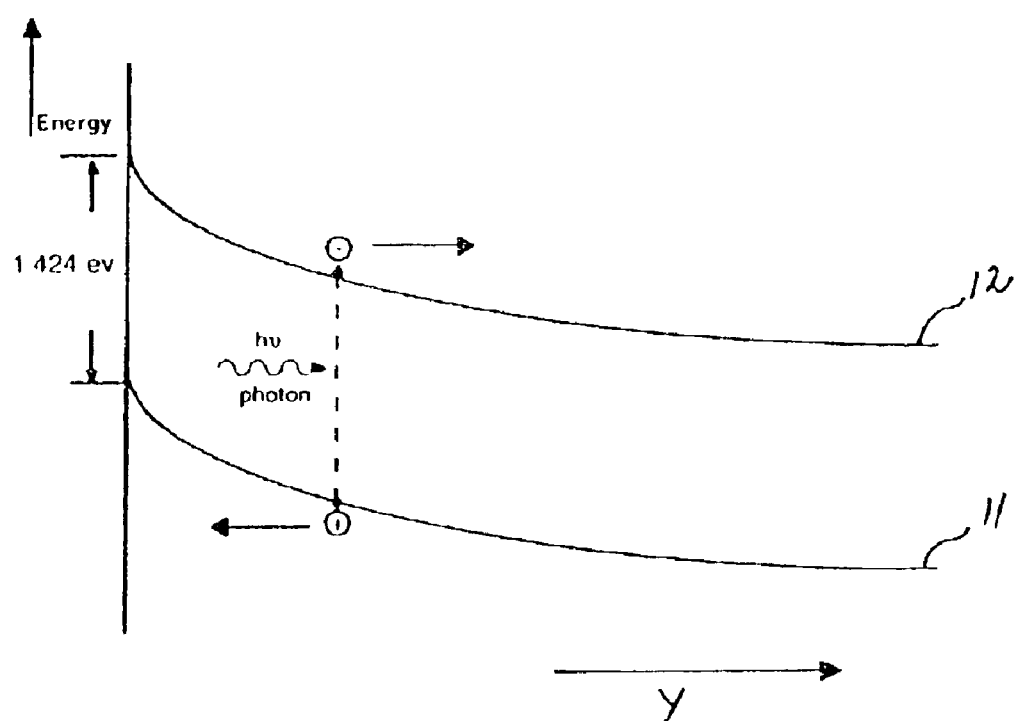
FIG. 4 is a schematic diagram showing the energy gap for GaAs.

FIG. 4 shows the energy gap for GaAs, conduction, and valence band edges as a function of position in the direction y (parallel to the layers of an n-type $GaAs/Al_xGa_{1-x}As$ multi-layer structure near an exposed surface). As a result of illumination of the structure, an electric field is formed, which sweeps optically generated holes and electrons, respectively, towards and away from the surface.

A steady-state positive (hole) charge is maintained at the surface under constant illumination. Similarly, a p-type $GaAs/Al_xGa_{1-x}As$ multilayer structure will yield a steady-state negative (electron) charge at the surface under illumination. As seen from FIG. 4, at room temperature, the energy gap for GaAs is 1.424 eV and is the difference between the energy levels for the conduction band 12 and the valence band 11.

The calculations show that at room temperature the energy gap $E_g$ for $Al_xGa_{1-x}As$ is computed according to equation (1)

$$E_g = 1.424 + 1.247x, \quad (1)$$

wherein x is below 0.45.

Thus, for x=0.16 (the lowest preferred value for x as discussed above) $E_g$ equals 1.624 eV.

For x above 0.45, the energy gap is computed according to equation (2):

$$E_g 1.900 + 0.125x + 0.143x^2 \quad (2)$$

Thus, for x=0.8, $E_g$ equals 2.092 eV. The optical absorption edge in the structure can be altered by varying the GaAs layer width (due to quantum confinement effects), or by changing its composition to $Al_yGa_{1-y}As$, where y<x.

In view of the preceding discussion it is clear that for the preferred superlattice structure of this invention, the energy gaps and corresponding wavelengths of the source of illumination are as shown in Table 1 below.

Table 1

Energy gap levels and corresponding wavelengths of the source of illumination for the layers of the preferred embodiment of the superlattice of this invention

TABLE 1

Energy gap levels and corresponding wavelengths of the source
of illumination for the layers of the preferred embodiment of
the superlatice of this invention

| Layer | Energy gap, $E_g$ eV | Wavelength, nm. |
|---|---|---|
| GaAs | 1.424 | 870 |
| Al, Ga, As | between 1.673 (x = 0.2) and 2.092 (x = 0.8) | between 741 (x = 0.2) and 593 (x = 0.8) |

In view of the foregoing, the preferred range of wavelengths used to activate the superlattice structure 100 is within a range of above about 741 nm and below about 870 nm, more preferably, below about 800 nm, and most preferably, about 750 nm. Illumination at wavelengths shorter than the lower limit of this range carries too much energy and will activate the $Al_xGa_{1-x}As$ layer which activation should be avoided. Conversely, illumination at wavelengths longer than the upper limit of this range does not carry enough energy to activate the GaAs layer. Without such activation the device will not work.

Figure 1A:
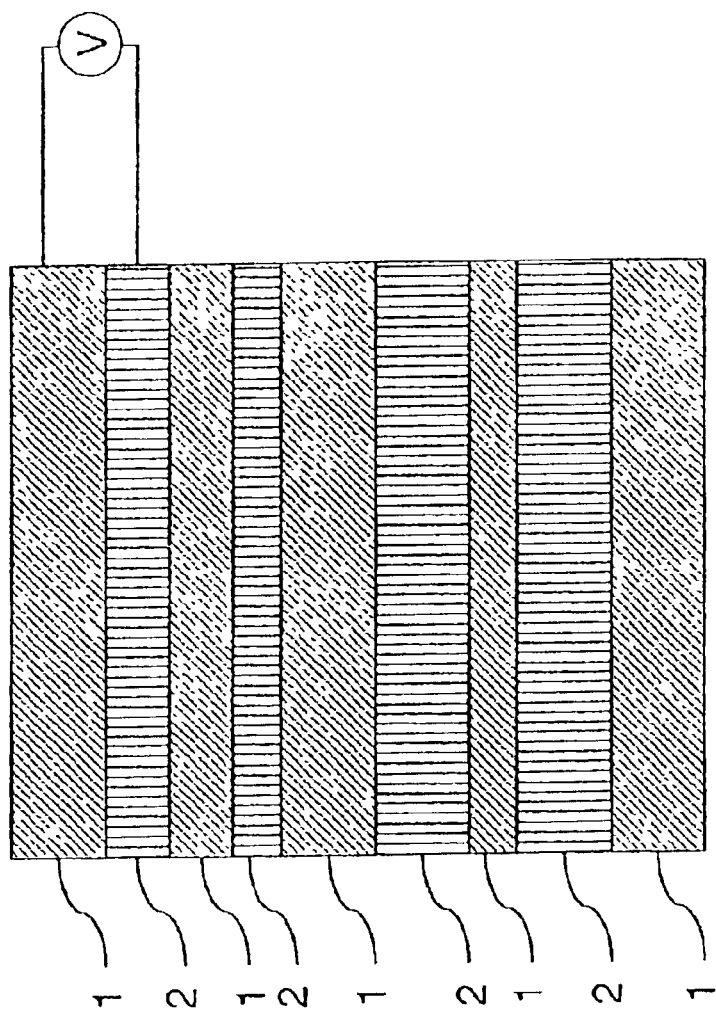
FIG. 1a is a schematic diagram showing a perspective view of a preferred multi-layer structure activated by the method of electrical biasing.

As an alternative, non-preferred method of activating the individual layers, electrical biasing is used, as shown on FIG. 1*a*. For this purpose, electrical current with voltage within a preferred range of between about 3 Volts and about 5 Volts is used. For illustrative purposes FIG. 1*a* shows that the voltage is applied only to one GaAs layer 1, but it should be understood that the voltage is to applied to every GaAs layer 1.

After the biological and/or chemical molecules have been trapped and concentrated on the surface of the superlattice, they are detected by one of existing analytical methods known to those skilled in the art, preferably by the method of fluorescence spectroscopy, or less preferably by the method of upconverting phosphor. In the alternative, the superlattice structure 100 can be incorporated into other devices such as surface acoustic wave (SAW) resonators, cantilever resonators or surface plasmon reflectors. The selective and switchable binding of the superlattice structures controlled by optical modulation (or use of another means), enables these devices to effectively detect the presence of particular bio-agents.

Finally, after the biological and/or chemical molecule was trapped and identified, it is released from the superlattice sidewall, for instance, by illumination with a different wavelength of light, or wavelength with an energy greater than the bandgap of AlGaAs spacer layers. Generally, the wavelength used for this purpose is shorter than about 500 nanometers. Following such detachment of the biological and/or chemical agent, the device is ready to be used again.

Having described the invention in connection with several embodiments thereof, modification will now suggest itself to those skilled in the art. As such, the invention is not to be limited to the described embodiments except as required by the appended claims.

We claim:

1. A concentrater of biological and/or chemical materials comprising an engineered superlattice structure, wherein said structure is fabricated out of semiconducting materials, said structure having a surface with surface binding properties for binding and releasing said biological and/or chemical materials.

2. The concentrator as claimed in claim 1, wherein said surface binding properties are controlled by optical illumination or electrical biasing.

3. The concentrator as claimed in claim 1, wherein said semiconducting materials comprise group III-group V semiconducting materials, or group IV-group IV semiconducting materials.

4. The concentrator as claimed in claim 1, wherein said biological and/or chemical materials comprise phosphoglycerides, deoxyribonucleic acid, or ribonucleic acid.

5. The concentrator as claimed in claim 1, wherein said superlattice structure comprises a plurality of alternating layers made of elemental semiconducting materials and binary or ternary semiconducting materials of said semiconducting materials or wherein said superlattice structure comprises a plurality of alternating layers made of binary semiconducting materials and binary or ternary semiconducting materials of said semiconducting materials.

6. The concentrator as claimed in claim 5, wherein said layers made of elemental semiconducting materials comprise a material selected from group IV materials.

7. The concentrator as claimed in claim 5, wherein said superlattice structure comprises alternating layers of binary and ternary semiconducting materials and said binary semiconducting materials are selected from the group consisting of gallium-arsenide, gallium-phosphide, silicon-germanium, silicon-carbon, gallium-antimonide, iridium-arsenide, indium-phosphide, indium-antimonide, aluminum-arsenide, and aluminum-antimonide, and said ternary semiconducting materials are selected from the group consisting of aluminum-gallium-arsenide, silicon-germanium-carbon, indium-gallium-phosphide, indium-gallium-arsenide, indium-aluminum-arsenide, aluminum-gallium-arsenide, and aluminum-gallium-antimonide.

8. The concentrator as claimed in claim 3, wherein said superlattice structure comprises a plurality of alternating layers of silicon and silicon-germanium, silicon and silicon-carbon, silicon and silicon-germanium-carbon, or silicon-germanium and silicon-carbon semiconducting materials.

9. The concentrator as claimed in claim 5, wherein said superlattice structure has a thickness within a range of between about 1 micrometer and about 5 micrometers.

10. The concentrator as claimed in claim 5, wherein each layer of said alternating layers has a thickness within a range of between about 3 Angstroms and about 10 Angstroms.

11. The concentrator as claimed in claim 5, wherein said structure is fabricated by a method of molecular beam epitaxy (MBE).

12. The concentrator as claimed in claim 5, wherein said surface has edges, said edges having a mesa structure or a graded structure.

13. The concentrator as claimed in claim 12, wherein said edges are formed by a method of wet-chemical etching or by a method of reactive ion etching.

\* \* \* \* \*